US00PP23607P2

(12) United States Plant Patent
Bradford

(10) Patent No.: US PP23,607 P2
(45) Date of Patent: May 21, 2013

(54) NECTARINE TREE NAMED 'PEARLICIOUS VI'

(50) Latin Name: *Prunus persica*
Varietal Denomination: Pearlicious VI

(76) Inventor: Lowell Glen Bradford, Le Grand, CA (US)

( * ) Notice: Subject to any disclaimer, the term of this patent is extended or adjusted under 35 U.S.C. 154(b) by 11 days.

(21) Appl. No.: 13/374,008

(22) Filed: Dec. 8, 2011

(51) Int. Cl.
*A01H 5/00* (2006.01)

(52) U.S. Cl.
USPC ..... Plt./188

(58) Field of Classification Search ..... Plt./188
See application file for complete search history.

(56) References Cited

U.S. PATENT DOCUMENTS

PP10,871 P 4/1999 Bradford
PP14,242 P2 10/2003 Bradford

*Primary Examiner* — Kent L Bell

(57) ABSTRACT

The present invention relates to a new and distinct variety of nectarine tree, *Prunus persica*, broadly characterized by a medium size, vigorous, hardy, self-fertile, productive and regular bearing tree. The variety blooms between the early and mid season and requires about 525 chilling hours. The fruit matures under the ecological conditions described in early July, with first picking on Jul. 2, 2011. The fruit is very large in size, globose in shape, clingstone in type, firm and melting in texture, white in flesh color, mostly red in skin color, and a balance of acid and sugar in flavor.

1 Drawing Sheet

Botanical classification: *Prunus persica.*
Variety denomination: 'Pearlicious VI'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of nectarine tree, which has been denominated varietally as 'Pearlicious VI'.

The present variety was hybridized by me in 2003 as a first generation cross using an unnamed yellow flesh nectarine selection designated by code number '6P740' (unpatented) as the selected seed parent and 'Diamond Pearl' (U.S. Plant Pat. No. 14,242) white flesh nectarine as the selected pollen parent. The fruit of this cross was gathered in the spring of 2003, and the seeds were removed from the fruit, germinated, stratified, and grown as seedlings on their own root in my greenhouse. Upon reaching dormancy the following winter, the seedlings were transplanted as a group to a cultivated area of my experimental orchard located near Le Grand, Calif., in Merced County (San Joaquin Valley). During the fruit evaluation season of 2007 I selected the present variety as a single tree from the group of seedlings described above. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, '6P740' nectarine by producing nectarines that are mostly red in skin color, clingstone in type, and firm in texture, but is quite distinguished therefrom by producing nectarines that are white in flesh color instead of yellow and that ripen about twenty-five days later.

The present variety is similar to its pollen parent, 'Diamond Pearl' nectarine (U.S. Plant Pat. No. 14,242) by producing fruit that is clingstone in type, white in flesh color, and firm in texture, but is quite distinguished therefrom by producing fruit that is larger in size and that matures about seventeen days later.

The present variety is most similar to 'Kay Pearl' (U.S. Plant Pat. No. 10,871) nectarine by producing nectarines that are white in flesh color, mostly red in skin color, and that typically mature in late June to early July, but is distinguished therefrom by having reniform instead of globose leaf glands and by producing fruit that is clinstone instead of freestone in type, that is much larger in size, and that is lightly acidic instead of sub-acidic in flavor.

SUMMARY OF VARIETY

In summary, the present nectarine variety is characterized by a medium size, vigorous, hardy, self-fertile, productive and regular bearing tree. The variety blooms between the early and mid season and requires about 525 chilling hours. The fruit matures under the ecological conditions described in early July, with first picking on Jul. 2, 2011. The fruit is very large in size, globose in shape, clingstone in type, firm and melting in texture, white in flesh color, mostly red in skin color, and a balance of acid and sugar in flavor.

DRAWING

The accompanying photograph consists of four whole fruits positioned to display the characteristics of the skin color and form, one divided fruit to reveal the flesh and stone, a typical young tip shoot, characteristic leaves, and two insets to reveal buds and a blossoms.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jul. 7, 2011, on the original tree during its eighth growing season. The blossom and flower descriptions were made the previous blooming season. All major color code designations are by reference to the Inter-Society Color Council, National Bureau of Standards. Common color names are also used occasionally.

PARENTAGE

Seed parent: '6P740' nectarine (unpatented).

Pollen parent: 'Dimaond Pearl' nectarine (U.S. Plant Pat. No. 14,242).

TREE

Size: Medium, reaching and maintaining a height of 10' [3.05 m.] and a spread of 5' [1.52 m.] after eight growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase type.

Hardiness: Hardy with respect to central California winters.

Approximate chilling requirement: 525 hours.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Trunk:

- *Size.*—Medium, reaching a maximum diameter of 4¾" [120.7 mm.] after the eighth growing season.
- *Texture.*—Medium shaggy.
- *Bark color.*—A Dark grayish brown [62. d.gy.Br] and Deep brown [56. deep Br] variegation with Moderate orange yellow [71. m.OY] crevices.
- *Lenticels.*—Approximate Number Per Square Inch: 8. Color: Brilliant orange yellow [67. brill.OY]. Average Size: ¼" [6.4 mm.] to 7/16" [11.1 mm.]. Shape: Eye-shaped, elongated.

Branches:

- *Size.*—Diameter of a main scaffold is 3" [76.2 mm.] measured 12" above the crotch, diameter of a limb is 1½" [38.1 mm.] measured 12" above the first fork.
- *Texture.*—Smooth on first year wood, increasing roughness with age.
- *Color.*—Second Year Wood: Strong yellowish brown [74. s.yBr] with Strong yellow green [117. s.YG] permeating through.
- *Lenticels.*—Number Per Square Inch: About 60 on second year wood. Color: Light yellowish brown [76. l.yBr]. Average size: 1/64" [0.4 mm.] to 1/16" [1.6 mm.] on second year wood. Shape: Eye-shaped, elongated.

Leaves:

- *Size.*—Large. Average Length: 5⅝" [142.9 mm.]. Average Width: 1½" [38.1 mm.].
- *Arrangement.*—Alternate.
- *Thickness.*—Medium.
- *Form.*—Elliptical.
- *Apex.*—Acuminate.
- *Base.*—Acute with an average angle of 75 degrees.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Vein color.*—Light yellow green [119. l.YG].
- *Petiole.*—Average Length: ¼" [6.4 mm.]. Average Thickness: 1/16" [1.6 mm.]. Color: Strong yellow green [117. s.YG].
- *Stipules.*—Number: Usually 2 per leaf, up to 6 per growing tip. Average Length: ¼" [6.4 mm.]. Color: Dark olive green [126. d.OlG] becoming Deep reddish brown [41. deep rBr] with maturity.
- *Glands.*—Number: 1 to 4 per leaf. Position: Slightly alternate. Size: Medium. Form: Reniform. Color: Strong yellow green [117. s.YG] becoming Moderate yellow green [120. m.YG] with age.
- *Leaf buds.*—Pointed, medium in size.

Flower buds:

- *Hardiness.*—Hardy, with respect to central California winters.
- *Diameter.*—Typically ⅜" [9.5 mm.] 1 week before bloom.
- *Length.*—Typically ⅝" [15.9 mm.] 1 week before bloom.
- *Form.*—Not appressed.
- *Surface.*—Pubescent.
- *Tip color.*—Moderate purplish pink [250. m.pPk].

Flowers: Perfect, complete, perigynous, usually a single pistil, about thirty stamens, five sepal and petal locations alternately positioned.

- *Type.*—Showy, large.
- *Average flower diameter.*—1 15/16" [49.2 mm.].
- *Number of petals.*—Mostly five, extra petal fragments or double blossoms are commonly observed.
- *Petal shape.*—Circular to oval.
- *Petal margin.*—Entire, quite wavy.
- *Average petal diameter.*—13/16" [20.6 mm.].
- *Average petal length.*—¾" [19.1 mm.].
- *Petal apex.*—Rounded.
- *Petal base.*—Rounded to somewhat truncate.
- *Petal color.*—Light purplish pink [249. l.pPk] toward the apex, Deep purplish pink [248. deep pPk] toward the base on both sides.
- *Anther color.*—Moderate red [15. m.R] over a Light yellow [86. l.Y] center at bloom onset.
- *Stigma color.*—Light greenish yellow [101. l.gY].
- *Sepal color.*—Dark purplish red [259. d.pR] on the outer surface.
- *Sepal length.*—¼" [6.4 mm.].
- *Sepal width.*—3/16" [4.8 mm.].

*Sepal apex.*—Rounded to elliptical to match the sepal length and width.
*Sepal margin.*—Fairly smooth.
*Average pistil length.*—13/16" [20.6 mm.].
*Average stamen length.*—½" [12.7 mm.].
*Fragrance.*—Moderate.
*Blooming period.*—Early to medium, with 'Spring Bright' (U.S. Plant Pat. No. 7,507) nectarine.
*Onset of bloom.*—One percent on Feb. 20, 2011.
*Date of full bloom.*—Mar. 2, 2011.
*Duration of bloom.*—One to two weeks, dependent on ambient temperature.
*Number per cluster.*—1 to 3 with single flowers most common.

FRUIT

Maturity when described: Firm ripe, Jul. 7, 2011.
Date of first picking: Jul. 2, 2011.
Date of last picking: Jul. 16, 2011.
Size: Uniform, very large.
*Average diameter axially.*—3" [76.2 mm.].
*Average diameter across cheek plane.*—3 3/16" [81 mm.].
*Average diameter across suture plane.*—3 5/16" [84.2 mm.].
*Typical weight.*—10.3 ounces [292 grams].
Form: Uniform, globose, slightly compressed axially.
*Longitudinal section form.*—Circular.
*Transverse section through diameter.*—Circular.
Suture: An inconspicuous line located in a shallow groove that extends from the base, continues along the side, and ends just past the pistil point.
*Near the base.*—A shallow groove.
*Along the side.*—A line.
*Near the apex.*—A shallow groove.
Ventral surface: Rounded strongly, lipped toward the base and apex.
Lips: Slightly unequal.
Cavity: Flaring, elongated in the suture plane, suture showing on one side, Pale yellow green [121. p.YG] stem markings typical.
*Depth.*—15/16" [23.8 mm.].
*Breadth.*—1 3/16" [30.2 mm.].
Base: Rounded, somewhat cordate if viewed parallel to the suture.
Apex: Rounded, cordate if viewed parallel to the suture.
Pistil point: An inconspicuous Dark brown [59. d.Br] dot, negligible in length, depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Nonastringent.
*Tendency to crack.*—None observed in a dry season.
*Color.*—Dark red [16. d.R] over a Moderate red [15. m.R] background with heavy Pale yellow green [121. p.YG] freckling mostly toward the apex.
Flesh:
*Color.*—Greenish white [153. gWhite] throughout with Pale yellow green [121. p.YG] fibers next to the stone.
*Surface of pit cavity.*—Covered with Brilliant yellow green [116. brill.YG] broken fibers when twisted from the stone.
*Amygdalin.*—Moderate.
*Juice.*—Moderate, rich.
*Texture.*—Firm, crisp, meaty.
*Fibers.*—Few, fine, tender.
*Ripens.*—Fairly evenly, earliest at the apex.
*Flavor.*—A tasty balance of sugar with light acid and a hint of traditional nectarine flavor, typically 16 to 18 brix.
*Aroma.*—Moderate.
*Eating quality.*—Very good.

STONE

Type: Clingstone.
Form: Oval.
Hilum: Narrow, oval.
Base: Acute.
Apex: Acute.
Sides: Equal.
Surface: Irregularly furrowed toward the apex, pitted toward the base.
Ridges: Rounded.
External color: Brownish orange [54. brO].
Pit wall color when cracked: Light yellow green [119. l.YG].
Cavity surface color: Deep yellow green [118. deep YG].
Average pit wall thickness: 5/16" [7.9 mm.].
Average width: 1 1/16" [27 mm.].
Average length: 1 9/16" [39.7 mm.].
Average breadth: ⅞" [22.2 mm.].
Tendency to split: None observed.
Kernel:
*Form.*—Oval.
*Skin color.*—Pale yellow [89. p.Y] when first removed.
*Pellicle color.*—Light yellow [86. l.Y].
*Vein color.*—Pale greenish yellow [104. p.gY].
*Taste.*—Bitter.
*Viable.*—Yes.
*Average width.*—9/16" [14.3 mm.].
*Average length.*—¾" [19.1 mm.].
*Amygdalin.*—Moderate.

USE

Market: Fresh market and long distance shipping.
Keeping quality: Good. Fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'Kay Pearl' (U.S. Plant Pat. No. 10,871) nectarine by producing nectarines that are white in flesh color, mostly red in skin color, and that typically mature in late June to early July, but is distinguished therefrom by having reniform instead of globose leaf glands and by producing fruit that is clinstone instead of freestone in type, that is much larger in size, and that is lightly acidic instead of sub-acidic in flavor.

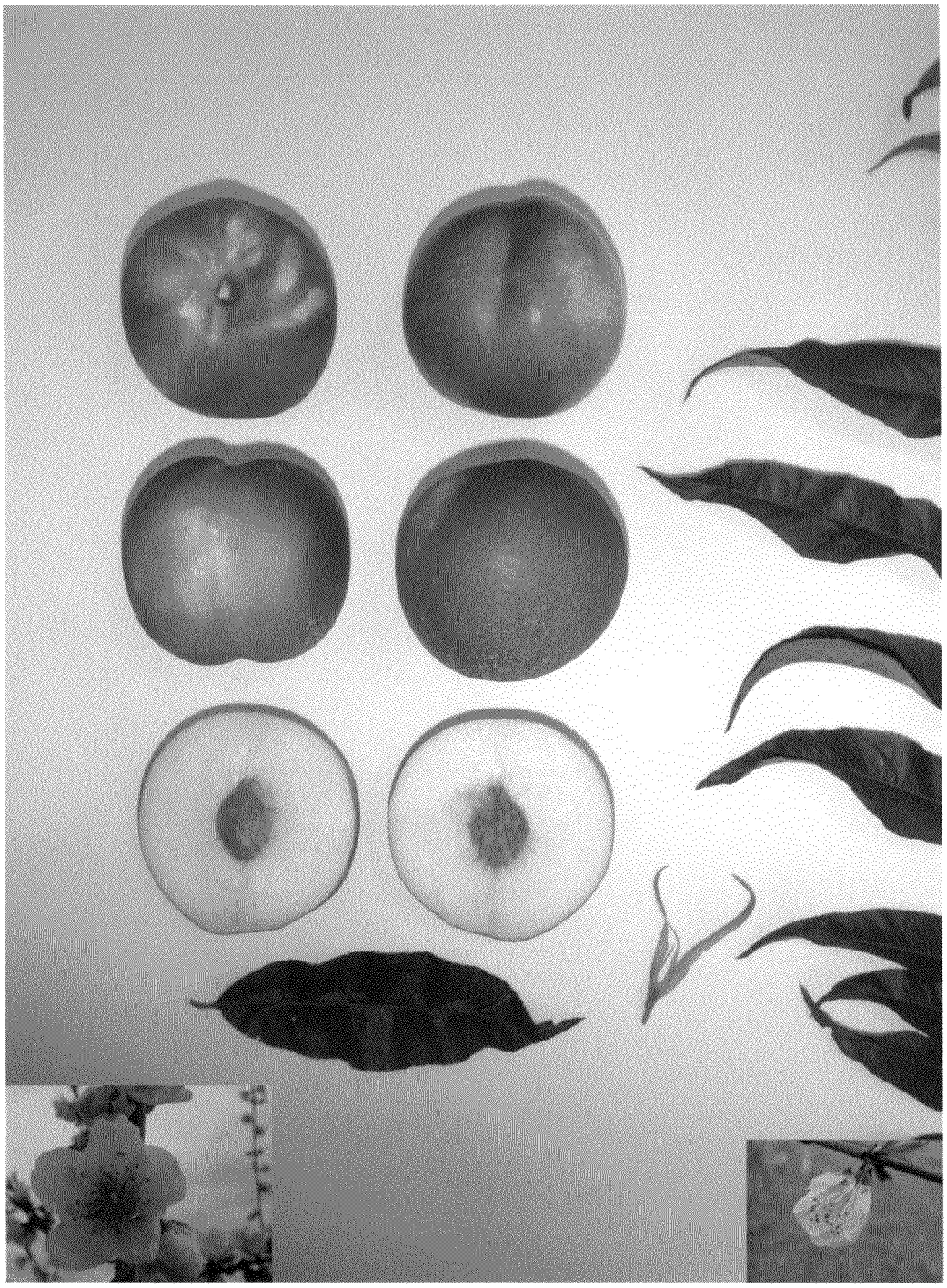

* * * * *